United States Patent [19]

Hall et al.

[11] Patent Number: 4,698,311
[45] Date of Patent: Oct. 6, 1987

[54] PARTICLE WASHING AND SEPARATION METHOD

[75] Inventors: Shelby J. Hall, Stewartsville; David J. Olekna, Annandale; Donald M. Davies, Jr., Raritan, all of N.J.

[73] Assignee: Ortho Diagnostic Systems Inc., Raritan, N.J.

[21] Appl. No.: 676,973

[22] Filed: Oct. 30, 1985

[51] Int. Cl.$^4$ .................. G01N 1/00; B01D 33/02; B04B 5/02

[52] U.S. Cl. .................. 436/10; 210/789; 210/927; 436/16; 494/16

[58] Field of Search .............. 210/768, 772, 780, 781, 210/782, 787, 789, 927; 436/10, 16, 63; 422/72, 101, 102; 494/16, 20, 21

[56] References Cited

U.S. PATENT DOCUMENTS

| | | | |
|---|---|---|---|
| 1,907,605 | 5/1933 | Stigen | 422/72 X |
| 3,406,121 | 10/1968 | Jones | 436/10 |
| 4,106,907 | 8/1978 | Charlton et al. | 422/72 X |
| 4,308,232 | 12/1981 | Crouther et al. | 210/927 X |
| 4,486,315 | 12/1984 | Teipel | 210/927 X |

*Primary Examiner*—Richard V. Fisher
*Assistant Examiner*—W. Gary Jones

[57] ABSTRACT

A device is described for preparing a standardized concentration of washed particles suspended in a fluid. The preferred method is directed to the preparation from whole blood specimens of a standardized concentration of washed red cells in isotonic solution using a device comprising a test tube formed at the bottom end with a nipple-like receptacle having a predetermined volumetric capacity. Whole blood is mixed with isotonic solution in the device which is then centrifuged causing the red cells to be first washed and then packed into the receptacle. The liquid contents of the device are then decanted without disturbing the packed red cells. Thereafter, the red cells are reconstituted to the desired concentration by adding isotonic solution to a predetermined level in the tube and mixing the cells into the isotonic solution.

4 Claims, 2 Drawing Figures

PARTICLE WASHING AND SEPARATION METHOD

FIELD OF THE INVENTION

This invention relates to a device and method for preparing a standardized concentration of washed particles suspended in a fluid. Preferably, the invention relates to the preparation of a standardized suspension of washed red blood cells from a whole blood specimen.

BACKGROUND OF THE INVENTION

It has long been recognized that it is necessary to separate blood samples into their respective component parts, such as the cellular components and plasma or serum, for test purposes and other medical applications. For example, before a donor's red blood cells are tested for antigen-make up or evaluated for their compatibility with the recipient's serum prior to transfusion, they should be washed to remove proteins and resuspended in a known volume of an isotonic solution. It is well known that the separation of anticoagulated whole blood into its component parts can be effected by centrifugation whereby the red blood cells are forced under increased gravitational forces to the bottom of a centrifuged test tube thereby displacing plasma and other less dense components to higher levels. In those operations requiring merely the red blood cell layer, typically the plasma portion is decanted and the red blood cells are resuspended in a wash solution. Generally, the solution is a salt based solution. Resuspension of cells is generally accomplished by physical agitation so that any plasma which may have been trapped in intracellular spaces between the cells upon centrifugation is similarly resuspended into the solution. The solution containing the newly suspended red blood cells is then typically recentrifuged in order to repack the red blood cells together at the bottom of the tube and the supernate with the contaminating serum is again decanted. This operation of centrifugation and resuspension is generally repeated three times in order to maximize the washing of the red blood cells and remove serum which contains gamma globulin and complement components which could interfere with the Coombs Test yet still retain as many cells as possible. Although the standard recovery system results in a relatively clean population of red blood cells with minimal contamination by other elements present in the blood, there generally is a large loss of red blood cells of between 20 and 30% because of the numerous physical operations performed upon the red blood cells. Further, due to the nature of the physical operations required, automated procedures are difficult to institute and require complex, cumbersome and expensive equipment. In addition, the standard recovery systems require an average of five to six minutes per three wash cycles of the blood sample which puts an increased load upon the personnel and equipment resources when large numbers of samples must be handled.

As pointed out above, washed red blood cell suspensions are preferably used in many blood bank procedures. However, present techniques present two problems which are encountered by a technologist who wishes to prepare a suspension of washed red blood cells at some predetermined volumetric concentration. The first problem resides in the fact that the concentration of red blood cells present in various normal whole blood samples may range from 30% to 60% and may be much lower in anemic individuals. This large variation in the normal sample population prevents simple dilution from a sample of anticoagulated whole blood to prepare diluted red cells at a given predetermined concentration.

The second problem encountered by prior methods of washing red blood cells is one of time and mechanical manipulation. As pointed out above, the standard recovery systems require an average of five to six minutes per three wash cycles of the blood sample. In contrast thereto, the present method enables the red blood cells to be washed effectively and to be reconstituted to the desired percentage within less than 2 minutes.

A number of blood separation devices have been disclosed in the literature.

U.S. Pat. No. 3,932,277 to McDermott et al., directed to the separation of blood fractions, describes a system of tubes, one insertable into the other, whereby one tube inserts a barrier to separate the serum from the red blood cells after centrifuging in an attempt to prevent the mixing of the cells and the serum during decantation of the serum supernatant. During the insertion of the inner tube whereby the barrier is placed between the aforementioned portions, it is possible to have the serum filtered as it passes into the interior of the inner tube. Thus, this invention is directed towards the recovery of serum and requires great care in the placement of the barrier at the surface of the compacted red blood cell portion so as to avoid inadvertent mixing at that interface. Once in place, the barrier will prevent the removal of the red blood cells upon decantation of the serum. Thus, the barrier defeats a technician interested in working with the red blood cell layer from obtaining that cell layer. Devices, such as are disclosed in U.S. Pat. Nos. 3,799,342; 4,035,294; 4,244,694; 4,294,707; 3,687,296; 3,960,727 and 3,799,342 like the above McDermott et al. patent, are also primarily intended to facilitate recovery of the mother solution portion of the resuspension rather than the washing and suspension of the particles.

U.S. Pat. No. 3,914,985 to von Behrens is directed to a device for accurately measuring the packed mass of minor constituents of fluids, particularly whole blood, platelet-rich plasma and other body fluids. The device is particularly useful in hematology for determining the packed cell volume of platelets, lymphocytes and granularcytes. However, von Behrens makes no attempt to provide any washing and collecting of red blood cells. In fact, von Behrens states in column 7, line 29 that "unwanted cells (erythrocytes) will be disposed of entirely in the lower portion of the tube." This contrasts with one object of the present invention which is to prepare packed washed red cells and thereafter to prepare standardized concentrations thereof suspended in a compatible solution.

U.S. Pat. No. 3,075,694 to Anderson relates to a device for the separation of particles of different sizes or densities suspended in a liquid. There is, however, no disclosure therein concerning the washing of red blood cells or the reconstitution thereof in a compatible fluid.

U.S. Pat. No. 3,677,710 to Hirsch is directed to an apparatus for automatically performing the Coomb's antihuman globulin test in a continuous flow system. A techique is disclosed which permits continuous washing of the cells that are to be reacted with the Coomb's serum. This technique involves gravitational settling and separation of aggregated cells from a supernatant material. The Hirsch apparatus is quite complex and does not involve centrifugation. The present method, on the other hand, is a batch process and it is carried out in a relatively simple and inexpensive manner and yet provides fast, effective washing and resuspension of the red cells.

U.S. Pat. No. 3,858,795 to Joyce is directed to a method for washing blood cells by forcing the cells to the bottom of a stationary liquid in a container, where the liquid has a greater density at the bottom of the container than at the top. However, there is no disclosure therein of any device for preparing standarized concentrations of washed red cells.

U.S. Pat. No. 4,435,293 to Graham Jr. et al. relates to a particle washing system wherein in a preferred embodiment the fluid containing the desired particles is placed within an inner tube having near the bottom thereof an orifice with a diameter at least equal to that of the diameter of the particles, an air vent and, wherein the inner tube is positioned within an outer tube having a fluid with a density at least equal to that of the solution containing the particles to be separated within the inner tube but less than that of the particles. The application of centrifugal force to the particles directed toward the bottom of the outer tube causes the particles to move through the orifice and through the outer solution contained within the outer tube so that the particles are collected from the inner solution, washed by the outer solution and subsequently sedimented at the bottom of the outer tube. The device of Graham Jr. et al. does not disclose a method for obtaining a standarized concentration of red cells.

U.S. Pat. No. 4,436,631 to Graham Jr. et al., which patent is a continuation-in-part of the above-discussed U.S. Pat. No. 4,435,293, is similar thereto, and also does not disclose a method for obtaining a standardized concentration of red cells.

It is an object of the present invention to permit the rapid separation of particles from a solution in a "onestep" operation. It is another objective that during the separation of the particles from the solution containing the particles, the particles are washed so as to remove any non-specific serum coating and to dilute any solute drag. It is yet another objective of the present invention that these objects be accomplished in a simple system capable of economical production and employable within simple, inexpensive centrifuges commonly available. It is still yet another objective that the apparatus and methodology of the present invention be capable of replacing expensive automated cell washers presently available. Another object of the present invention is to permit a laboratory technologist to rapidly prepare standardized suspensions (with respect to concentration) of washed, red blood cells from whole blood specimens, with minimal technical manipulation. It is still another object of the present invention to provide an apparatus so that a known volume of "packed" red cells can be deposited into a receptacle, despite the fact that the concentration of red blood cells present in various normal whole blood samples may range from 30 to 60%. It is a further object of the present invention to provide a device wherein unwanted excess cells may be readily removed without disturbing desired cells.

It is yet a further object of the present invention to provide apparatus which permits facile production of a variety of cell concentrations. These any other objectives will readily become apparent to those skilled in the art in light of the teachings herein set forth.

SUMMARY OF THE INVENTION

In accordance with the objects and principles of the present invention, there is provided a device for preparing a standardized concentration of particles from a mother solution, comprising a tube for receiving and containing the mother solution containing the particles. The tube has receptacle means at the bottom thereof for receiving a predetermined volume of particles upon application of centrifugal force, whereby unwanted particles and mother solution may be removed and said predetermined volume of particles may be resuspended in a suspending fluid to a standardized concentration.

Preferably the receptacle means comprises a nipplelike receptacle formed in the bottom end of the tube. The tube and the receptacle preferably have common inner walls, the inner wall of the bottom end of the tube funneling down toward the top end of the inner wall of the receptacle.

When a liquid suspension of particles is placed in the tube and the latter is subjected to centrifugation, the receptacle becomes packed with the particles, the diameter of the top end of the receptacle being sufficiently small so that the packed particles will not be disturbed even when the tube is up-ended and the liquid contents of the tube are decanted.

In accordance with a preferred embodiment, the present device is used for preparing a standardized concentration of washed, red blood cells. Since the shape and size of human red cells is known and relatively uniform among individual adults, the number of red cells retained in the receptacle following centrifugation and decanting will be very similar from specimen to specimen. Thus, when the device of the present invention is to be centrifuged in a standard centrifuge normally used in this field, in order for the red cells to be properly packed into the receptacle, it can be calculated that the diameter at the top end of the receptacle should be between 2 and 4 millimeters and the volumetric capacity of the receptacle should be between 30 and 50 microliters but preferably about 40 microliters. This volumetric capacity of the receptacle is appropriate for use in a tube having a length of between about 68 millimeters and 90 millimeters and an external diameter of between 9 and 13 millimeters, in order to obtain red blood cells at concentrations, after resuspension of between 1% and 5% v/v.

In accordance with a further embodiment of the present invention, graduations are marked on the tube, so that by filling the tube with isotonic solution, when the receptacle contains packed red cells, a suspension of cells at a variety of predetermined concentrations may be prepared, such preferred concentrations being those generally employed in various blood banking procedures and including between 1% and 5% v/v.

In the preferred embodiment of the device of the present invention, the tube and the receptacle are symmetrically arranged so that they possess a common, longitudinal axis. Although the receptacle in the nipple is preferably of tubular shape, it could nevertheless be trapezoidal, conical or possess some other preferably symmetrical geometric form capable of holding between 30 and 50, preferably about 40 microliters of packed red blood cells, also provided that the diameter of the top of the receptacle is between 2 and 4 millimeters.

In accordance with one embodiment of the present invention, there is provided a process for preparing standardized concentrations of particles from a mother solution utilizing the above-described device. The process comprises the steps of adding to the tube the mother solution containing the particles whose concentration is to be standardized. The tube containing the mother solution is then centrifuged, whereby the receptacle is filled with the particles. Thereafter the particles and mother solution not contained within the receptacle are separated from the particles contained within the receptacle. The latter particles are then resuspended with a predetermined volume of a suspending fluid, whereby a standardized concentration of particles in the suspending fluid is obtained.

Preferably a wash fluid is initially added to the tube together with the mother solution containing the particles so that the particles are washed during the centrifugation step.

In accordance with a preferred process of the present invention, standardized concentrations of washed red blood cells are prepared utilizing the above-described device. The process comprises mixing about 4 mls of an isotonic solution with between about 0.20 mls and 0.50 mls of whole blood in the tube and centrifuging the tube and contents for a sufficiently long period of time to cause the red blood cells from the whole blood to be washed and then packed into the receptacle. Preferably sufficient whole blood is utilized at the outset so that after the centrifuging step, the packed red cells completely fill the receptacle. After the centrifuging step, the contents of the tube above the top of the receptacle are removed, preferably by decanting. Thereafter, the washed and packed red cells in the receptacle are reconstituted to the desired concentration by adding isotonic solution to a predetermined level in the tube and then the cells are mixed into the isotonic solution. The device which is utilized preferably has graduations marked on the tube representing red cell concentrations, volume per volume, of between 1% and 5%. The reason for this is that the majority of commercially supplied antisera are optimized to work in test situations where the added red cell concentration is between 2% and 5%, volume per volume. Furthermore, for compatibility testing, the technical manual of AABB recommends washing the donor red cells and resuspending in saline to a 2% to 5% suspension. As pointed out in "Blood Transfusion in Clinical Medicine" by P. L. Mollison, page 488, published by Blackwell Scientific Publications, it is too inconvenient for workers to use suspensions which are more dilute than 2%.

BRIEF DESCRIPTION OF THE DRAWINGS

The objectives and principals of the invention and the preferred embodiments thereof will best be understood by reference to the accompanying drawings wherein.

DETAILED DESCRIPTION OF THE INVENTION AND BEST MODE

The present invention relates to a device for preparing packed washed particles as well as a method of preparing standardized concentrations of washed particles suspended in a fluid. The preferred method is directed to the preparation from whole blood specimens of standardized concentrations of washed red cells in isotonic solution using a device comprising a test tube formed at the bottom end with a nipple-like receptacle having a predetermined volumetric capacity. Whole blood is mixed with isotonic solution in the device which is then centrifuged causing the red cells to be first washed and then packed into the receptacle. The liquid contents of the device are then decanted without disturbing the packed red cells contained within the receptacle. Thereafter, the red cells are reconstituted to the desired concentration by adding isotonic solution to a predetermined level in the tube and mixing the cells into the isotonic solution.

Figure 1:
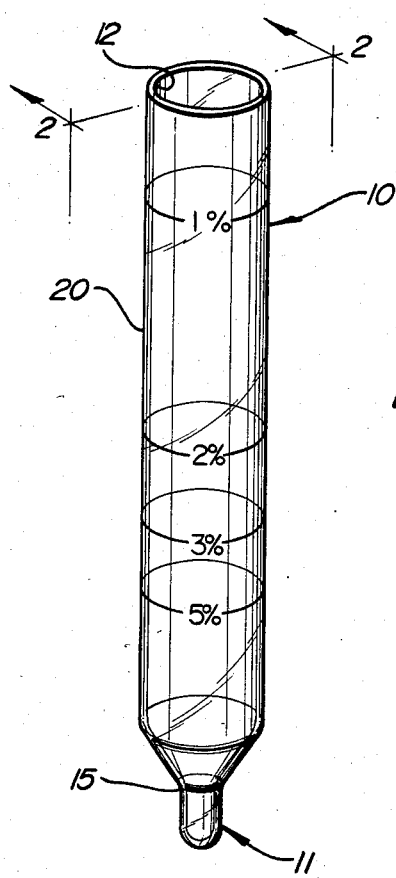
FIG. 1 is a side view of a preferred embodiment of the device of the invention.

FIG. 1 illustrates a preferred embodiment of the device 10. This embodiment consists of a plastic test tube 20 formed, most preferably, of low density polyethylene which have been initially admixed during formation of the tube, with a waxy slip agent. One suitable slip agent is "Slip Eze" which is a proprietary name for oleamide sold by Petrochemicals Co. Inc. Another suitable slip agent is known as "Mold Wiz" sold by Axel Plastics Research Laboratories, Inc. "Mold Wiz" is a proprietary blend of copolymers of cross-linked polyolefins and organic phosphate esters with modified fatty acids. The purpose of the slip agent is to reduce the amount of red cells adhering to the inner walls of the test tube 10 when the contents thereof are decanted and accordingly, any material equivalent to Slip Eze or Mold Wiz may be employed. Tube 20 is formed at the bottom thereof with a nipple-like receptacle 11. The receptacle 11 is preferably of a size and shape so that a known volume of "packed" red cells can be deposited therein under centrifugal force and any excess cells initially added will remain outside of the receptacle (i.e., above the top level of the receptacle indicated at 15). The device 10 of the invention is adapted to be used in connection with the standard centrifuges used for serological testing. These standard centrifuges, which are used throughout the industry, are adapted to function with test tubes of substantially standard height and width. Accordingly, tube 20 should have a length of between about 68 millimeters and 90 millimeters, preferably 75 millimeters and an external diameter of between 9 millimeters and 13 millimeters, preferably 12 millimeters. The volumetric capacity of the receptacle 11 may vary between 30 and 50 microliters but is most preferably about 40 microliters. The internal diameter of the receptacle 11 at the top end may vary between 2 and 4 millimeters but is most preferably about 3 millimeters. For practical reasons, the internal diameter of receptacle 11 is preferably greater than 2 millimeters so as to enable a Pasteur pipette to be inserted therein for aspirating the packed red cells into and out of the pipette, when the cells are to be resuspended.

Figure 2:
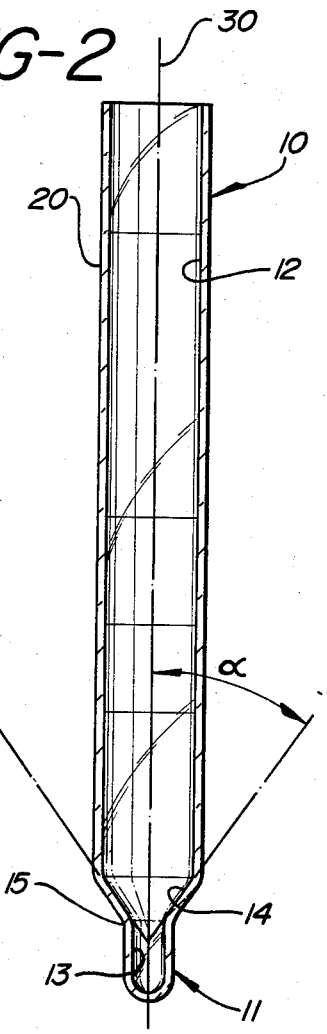
FIG. 2 is a cross-sectional view taken on the line 2—2 of FIG. 1.

It will be noted from FIG. 2 that the inner wall 12 of the tube 20 is common with the inner wall 13 of the receptacle 11, the wall 12 funneling into receptacle 11 so that the red cells, during centrifugation, may be smoothly directed towards said receptacle 11. The inner wall 14 at the bottom of tube 20 should funnel down towards the top end of the inner wall 13 of receptacle 11 so that the angle between said wall 14 and the central axis 30 of the tube 20 is between 30° and 45° and most preferably about 30°. Outside of this angular range, the red blood cells will not be properly funneled down into the receptacle 11.

The device 10 of the present invention separates red cells from serum components by centrifugation of a small sample of anticoagulated whole blood mixed with an isotonic solution which is placed within the tube 20.

Following centrifugation, the excess cells and contaminating serum proteins are removed by decanting and blotting. A volume of packed red blood cells is retained in the receptacle 11 by numerous physical forces. Since the volume of the receptacle 11 is constant, and the shape and size of human red cells is known and relatively uniform among individual adults, the number of red cells retained in the receptacle 11 following centrifugation and decanting will be very similar from specimen to specimen. Furthermore, because the plastic used in fabricating the tube is specifically chosen to minimize the adherence of excess red cells and serum protein to the walls 12 of the tube 20 during the decanting step, there are very few extraneous serum proteins remaining in the tube 20 following this step. In effect, the cells will have been effectively washed in one step only.

By adding varying amounts of saline solution to the device 10 which contains a fixed volume of packed red cells in receptacle 11, a suspension of washed red cells may be obtained at a known concentration. The concentration of red cells is adjusted by adding isotonic solution (preferably 0.9% saline) since the volume of packed red cells obtained will remain relatively constant. As will be seen from FIG. 1 of the drawings, graduations have been marked on the tube 20 to allow for the preparation of red cell suspensions at approximate concentrations of 1%, 2%, 3% and 5% volume per volume (v/v).

In the above procedures, blood having clotting inhibitors such as heparin, oxalate or citrate may be used. No special preparation of the patient is required prior to the collection of a specimen of whole blood. However, blood should be collected by approved medical techniques. When mixing whole blood with isotonic solution in the tube 20 prior to centrifuging, the order of the addition of whole blood or isotonic solution to the tube is irrelevant.

In carrying out the process of the present invention, sufficient isotonic saline solution is added to the tube 20 to fill it to the 1% mark, this being approximately 4 mls of saline. Thereafter, between 0.2 ml and 0.5 ml of mixed whole blood is added to the saline in the tube. Suitable volumes of whole blood can be obtained by adding 8 to 10 drops with a Pasteur pipette. The device 10 is then centrifuged for at least one minute at about 3400 r.p.m. However, speeds ranging between 1500 and 4000 r.p.m. may also be used and the duration of centrifuging may last for 5 minutes. After the centrifuge has been stopped, the device 10 is removed and the contents of the tube 20 are decanted. Excess liquid is blotted from the walls of the tube 20 by touching the lip of the inverted tube 20 to a paper towel or other absorbent material. Any adherent red cells remaining on the sides of the tube 20 can be removed by gently tapping the inverted tube on such absorbent material. If the receptacle 11 is completely filled to the point where the sides flair outward to join the base of the tube (namely, the point indicated at 15 on FIG. 2 of the drawings), a quantity of isotonic saline is added to the tube 10 so as to prepare a suspension of red blood cells at any desired concentration, such as at 2%, 3% or 5% v/v. The packed cells in the receptacle 11 can be resuspended in the isotonic solution by mixing on a vortex mixer or by repeatedly aspirating the cells into and out of a Pasteur pipette.

In the instance wherein the packed red cells do not fill receptacle 11 after the centrifuging step, it will be necessary to add additional whole blood to the same tube and repeat the procedure or repeat the entire procedure commencing with a larger initial quantity of whole blood.

It should be noted that the device of the present invention is preferably used once and then discarded because some plasma proteins coat the sides of the tube 20 and thus red cell adherence becomes more pronounced with each reuse of a single tube. Reuse would therefore result in increasingly inaccurate cell suspensions.

The device of the present invention will provide red cell suspensions that contain less than 0.2% of the initial whole blood protein.

An experiment was conducted in order to evaluate the use of different types of plastics to form the present device and to test the usefulness of the tubes 20 which were manufactured. In addition, the use of various quantities of additive substances (slip agents) were evaluated with these different plastics. The method for calculating the amount of hemoglobin remaining in each tube after the decanting step was as follows: Each device was filled with 4.0 ml of a suitable isotonic solution such as 0.9% sodium chloride in water. 200 µl of pooled whole blood (hematocrit=41) was added to each device which was then spun for 10 seconds in a Clay-Adams SEROFUGE at 3400 r.p.m. The devices were then removed and placed in a wooden rack. The rack was then inverted so that all the devices were inverted and the devices were drained for 20 seconds. Thereafter, 4.0 ml of distilled water were added per tube and mixed to lyse the red cells. The tubes were then spun to remove cell debris. Thereafter, 1.0 ml of the supernatant was added to 3.0 ml of distilled water. The amount of hemoglobin remaining in each tube was measured by standard procedures. The results are shown in the following Table I.

TABLE I

| Plastic Type | Lot & Source Type | Additive | Plastic:Additive (Amount of Additive Used) | Hemoglobin Remaining in Tube | | |
|---|---|---|---|---|---|---|
| Low Density Polyethylene | Bapolene 1072G | Slip EZE | 1000:1 | 1.145 | 1.066 | 1.105 |
| " | " | " | 1000:3* | .798 | .663 | .730 |
| " | " | " | 1000:5 | .741 | .619 | .680 |
| " | " | " | 1000:7 | .743 | .913 | .828 |
| " | " | Mold Wiz | 1000:1 | .815 | 1.246 | 1.030 |
| " | " | " | 1000:3 | .848 | .830 | .839 |
| " | " | " | 1000:7 | .755 | .846 | .800 |
| " | El Paso 127C | Slip EZE | 1000:1 | .957 | .875 | .916 |
| " | " | " | 1000:3 | .689 | .994 | .841 |
| " | " | " | 1000:5 | .758 | .871 | .814 |
| " | " | " | 1000:7 | .931 | .746 | .838 |
| " | " | Mold Wiz | 1000:1 | .954 | .861 | .907 |
| " | " | " | 1000:3 | .887 | .869 | .878 |
| " | " | " | 1000:5 | .897 | .721 | .809 |

TABLE I-continued

| Plastic Type | Lot & Source Type | Additive | Plastic:Additive (Amount of Additive Used) | Hemoglobin Remaining in Tube | | |
|---|---|---|---|---|---|---|
| " | " | " | 1000:7 | .916 | .895 | .905 |
| Polypropylene | — | " | 1000:1 | 1.055 | 1.121 | 1.088 |
| " | | " | 1000:5 | 1.054 | 1.072 | 1.063 |
| Styrene | — | " | 1000:1 | 1.054 | 1.161 | 1.107 |
| " | — | " | 1000:5 | .973 | 1.059 | 1.016 |
| High Density Polyethylene | — | " | 1000:1 | 1.091 | 1.132 | 1.111 |

Although the assay procedure was indirect, and measured the hemoglobin of all the cells remaining the tube, including the volume retained in the receptacle, two conclusions can be derived from the above tests:

1. Fewer red cells are retained in tubes made of low density polyethylene, compared with tubes made of polypropylene, styrene and high density polyethylene.

2. The use of slip agents (additives) increases the dumping efficiency of low density polyethylene. The dumping efficiency of tubes made of polypropylene, styrene and high density polyethylene is improved very little, if at all, with the addition of slip agents to the plastic.

It has been found that those slip agents, such as silicone, which do not remain within the walls of the tube, but which may tend to adhere, in part, to a pipette inserted in the tube, cause the problem of the wetting of the end of the pipette which would lead to drops which are too small, i.e., when a pipette tip has a slip agent adhering thereto and the pipette is used to extract a portion of the suspension in the tube, the pipette will dispense drops of suspension which are much smaller than those from an uncontaminated pipette. Thus it is preferred to incorporate slip agents into the walls of the tube rather than to apply surface coatings on the inner walls.

EXAMPLE

A 2% suspension in saline solution of washed red cells was prepared as follows: A device of the invention known as the "Ortho Cell Suspension Tube" which has a height of 80 millimeters and an external width of 12 millimeters was placed in an upright position and sufficient isotonic saline solution (consisting of 0.9% sodium chloride in water) was added to fill to the 1% mark on the tube. This was approximately 4 mls of saline.

While the filled tube was held upright, 0.2 mls of mixed whole blood was added to the saline in the tube, using a Pasteur pipette.

The filled "Ortho Cell Suspension Tube" was then placed into a Clay-Adams SEROFUGE centrifuge which is equipped to spin 12×75 millimeter tubes. The tube was then centrifuged for 60 seconds at 3400 r.p.m. (900–100 rcf).

After the centrifuge had been stopped, the "Ortho Cell Suspension Tube" was removed and the contents of the tube were decanted into a suitable waste container and excess liquid was blotted from the walls of the tube by touching the lip of the inverted tube to a paper towel placed on the laboratory benchtop. Any adherent red cells remaining on the sides of the tube were removed by gently tapping the inverted tube on a paper towel. The tube was then turned back to its upright position and the level of packed red cells present in the receptacle at the base of the tube was observed.

The receptacle was completely filled with packed red cells. Isotonic saline consisting of 0.9% sodium chloride in water was added up to the 2% mark. Thereafter, the packed red cells were resuspended in the saline by agitating the tube with a vortex mixer. At this point, the suspension which had been prepared was ready for use in any desired testing procedure.

Although the invention has been illustrated by the foregoing example, it is not to be construed as being limited to materials employed therein, but rather, the invention encompasses the entire generic area of particle separation and washing as hereinbefore disclosed. It will be apparent to the skilled worker in this field that various modifications and embodiments of this invention can be made without departing from the spirit and the scope thereof.

What is claimed is:

1. A process for preparing a standardized concentration of washed particles from a mother solution using a device comprising a tube having an open top end and a bottom end, there being a nipple-like receptacle having a predetermined volumetric capacity formed in said bottom end of said tube, said receptacle having an open top end and a closed bottom end, said tube and said receptacle having common inner walls, said inner wall of said bottom end of said tube funneling down towards the top end of said inner wall of said receptacle whereby, when a liquid suspension of particles is placed in said tube and said tube is subjected to centrifugation, said receptacle becomes packed with said particles, said process comprising the steps of:

providing said tube;

placing in said tube a preselected amount of said suspension of particles in said mother solution;

mixing a suitable amount of a wash fluid with said suspension;

centrifuging said tube and contents for a sufficiently long period to cause said particles to be washed and then to be packed into said receptacle;

stopping the centrifuge;

removing the contents of the tube above the packed particles in said receptacle without disturbing said packed particles;

adding a suspending fluid up to a predetermined level in said tube above said receptacle, and then mixing said packed particles into said suspending fluid so as to obtain a predetermined concentration thereof in the resultant suspension.

2. A process for preparing a standardized concentration of washed red blood cells using a device comprising a tube having an open top end and a bottom end, said tube having a central longitudinal axis, said tube having a length of between about 68 mm and 90 mm, and an external diameter of between 9 mm and 13 mm, there being a nipplelike receptacle formed in said bottom end of said tube, said receptacle having an open top end and a closed bottom end, the width of said receptacle at the top end thereof being between 2 and 4 mm, the volumetric capacity of said receptacle being between 30 and 50 microliters, said tube and said receptacle having common inner walls, said inner wall of said bottom end of said tube funneling down towards the top end of said inner wall of said receptacle at an angle to said central axis of said tube of between 30° and 45°, whereby when whole blood mixed with isotonic solution is placed in said tube and said tube is subjected to centrifugation, said receptacle becomes packed with red cells which will not be disturbed even when the tube is up-ended and the liquid contents of the tube are gently decanted, which process comprises:

mixing about 4 ml of an isotonic solution with between 0.20 ml and 0.50 ml of whole blood in said tube;

centrifuging said tube and contents for a sufficiently long period to cause the red blood cells from said whole blood to be washed and then packed into said receptacle;

stopping the centrifuge;

removing the contents of the tube above the top of said receptacle; and reconstituting said washed, packed cells in said receptacle to the desired concentration by adding isotonic solution to a predetermined level in said tube and mixing said cells into said isotonic solution.

3. The process of claim 2 wherein the removal of the contents of said tube above the top of the receptacle, after the centrifuging step, is accomplished by decanting.

4. The process of claim 2 in which the isotonic solution is saline solution.

* * * * *